United States Patent [19]

Levy

[11] 4,423,741

[45] Jan. 3, 1984

[54] MIDSTREAM SAMPLING OF CATHETERIZED LIQUID FLOW FROM A BODY CAVITY AND IMPROVED COUPLING THEREFOR

[75] Inventor: Norman Levy, Highland Park, Ill.

[73] Assignee: Plasco, Inc., Gurnee, Ill.

[21] Appl. No.: 360,409

[22] Filed: Mar. 22, 1982

Related U.S. Application Data

[63] Continuation of Ser. No. 111,591, Jan. 14, 1980, abandoned.

[51] Int. Cl.³ .............................................. A61B 10/00
[52] U.S. Cl. .................................... 128/768; 128/767; 604/323; 604/409; 604/249; 137/625.48; 137/625.68
[58] Field of Search ............... 128/760, 762, 763, 766, 128/768; 604/27, 30, 33, 43, 246, 249, 256, 262, 317, 323, 327, 335, 410, 409; 137/625.48, 625.68; 251/297

[56] References Cited

U.S. PATENT DOCUMENTS

| 389,652 | 9/1888 | Heltzle | 137/625.68 X |
|---|---|---|---|
| 3,459,174 | 8/1969 | Walker | 128/761 |
| 3,678,959 | 7/1972 | Liposky | 604/33 X |
| 3,774,591 | 11/1973 | Corbin et al. | 128/761 X |
| 3,823,716 | 7/1974 | Hale | 604/335 X |
| 3,830,225 | 8/1974 | Shinnick | 128/768 |

Primary Examiner—Kyle L. Howell
Assistant Examiner—Christine A. Fukushima
Attorney, Agent, or Firm—Norman Lettvin

[57] ABSTRACT

An improved method and apparatus for effecting midstream sampling of catheterized flow of liquid from a body cavity is effected through use of an improved coupling between sections of catheter tube means. The improved coupling includes a tubular cross-member that provides two pairs of oppositely extending tubular arms, a first pair of arms adapted to connect to the portions of the catheter tube means, and with a valve member constructed and arranged for selective reciprocal movement in the other pair of tubular arms and so as to permit usual drainage in one position or to provide, in said second position, means for effecting diversion of flow for effecting mid-stream sampling without separating portions of the catheter system that might permit contamination. In the second position, the constructions permit of effecting a backflow flushing of the body cavity, or application of medication, or an instrument, through the improved coupling into the body cavity. Means are provided to maintain the valve member in desired alignment with the cross-member.

9 Claims, 7 Drawing Figures

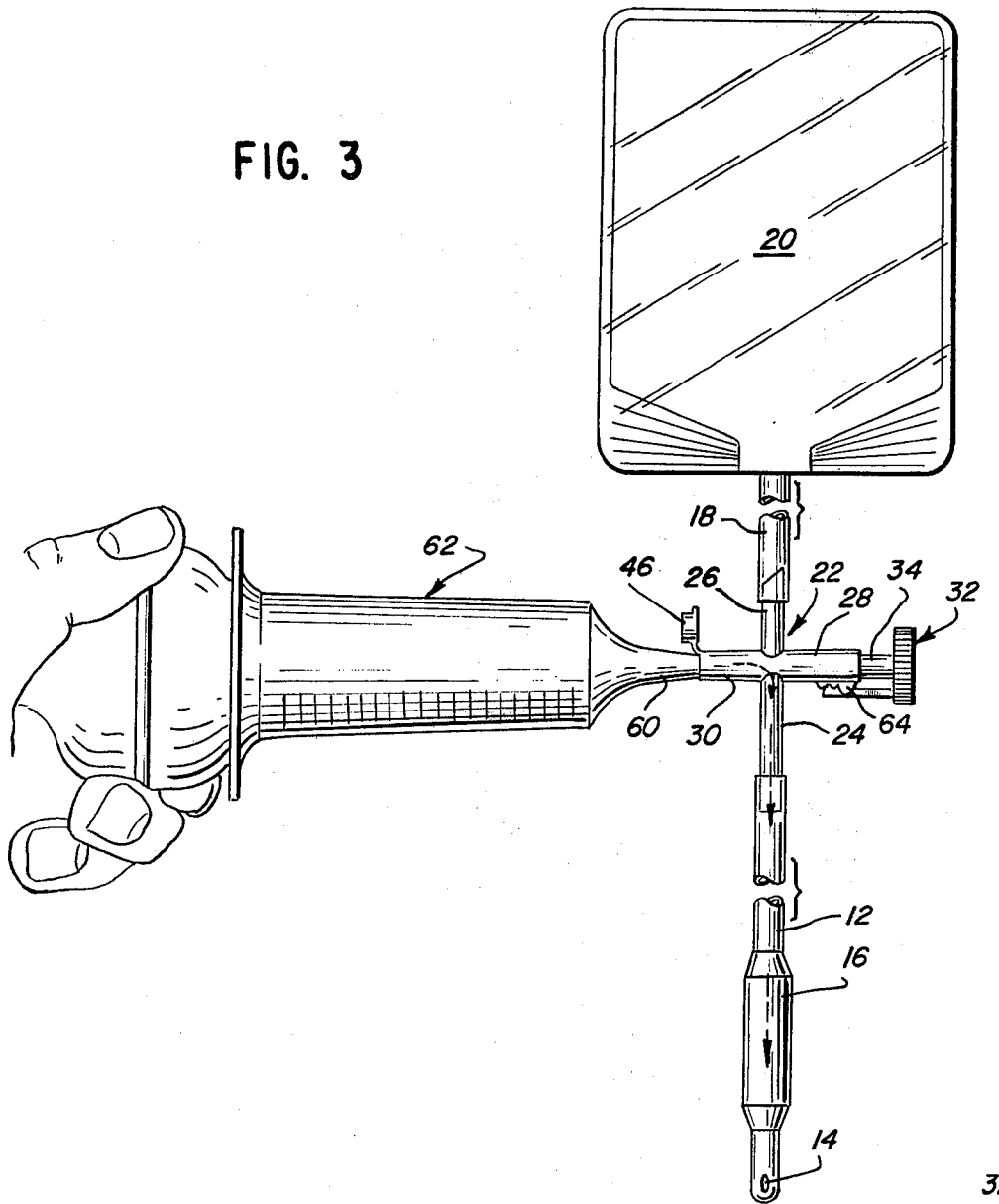
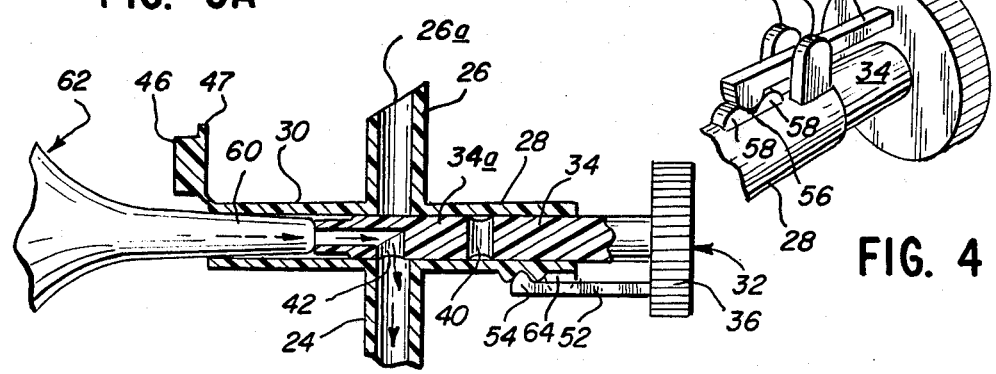

MIDSTREAM SAMPLING OF CATHETERIZED LIQUID FLOW FROM A BODY CAVITY AND IMPROVED COUPLING THEREFOR

This is a continuation of application Ser. No. 111,591, filed Jan. 14, 1980, now abandoned.

FIELD OF THE INVENTION

This invention relates to mid-stream sampling of catheterized flow of liquid from a body cavity, and to improved means for providing access to a catheterized body cavity for effecting irrigation, application of medication or the like.

BACKGROUND OF THE INVENTION

In catheterization for drainage of fluids from a body cavity, such as urethral catheterization, it is frequently necessary to sample the draining fluid, for purposes of providing a sample specimen of fluid for laboratory testing.

A closed system of catheterization is most desirable as it substantially precludes most contaminations that could occur if the system is opened for whatever reason. However, in urethral catheterization it is frequently necessary to obtain a mid-stream sample of urine for laboratory testing. At present, to obtain such a mid-stream liquid sample, the typical procedure is to separate the upstream catheter tube means from a downstream receiving tube means, permitting capture in a container or vial of a specimen of urine issuing from the free end of the catheter tubing means, or alternatively, a sample may be obtained by bleeding off a portion of the captured urine from the bag provided therefor, as disclosed in U.S. Pat. No. 3,823,716. In both of the foregoing procedures the capture system has been opened to ambient conditions and the possibility of contamination from such ambient conditions exists. This opening of a catheter system for sampling may be referred to as a dirty system because of the possibility of contamination.

It is also sometimes required to have access to the catheterized body cavity, such as for effecting a selective back flushing, or irrigation, of the body cavity that is catheterized, or for introducing a medicament, or air, or an instrument into the body cavity through the catheter. Again, the normal procedure with presently known equipment usually requires breaking the closed system to permit access to the cathetered body cavity through the catheter.

It is an object of this invention to provide an improved means for effecting mid-stream sampling of fluid being drained through a catheter, without the necessity of separating the segments of, or opening, the catheterization system.

It is another object of this invention to provide an improved and simplified means for effecting access to the catheterized body cavity, for purposes such as effecting irrigation of, or providing access to, the body cavity that has been catheterized.

It is a further object of this invention to provide an improved coupling and valving system for catheter systems, which is characterized by ease and simplicity of operation, by efficiency in effecting mid-stream sampling of the liquid flow, and/or in effecting irrigation of the catheterized body cavity, and which improved valving system is characterized by simplicity of operation and overall cost effectiveness.

Further objects of this invention will become apparent to persons skilled in the art from the following description of a preferred embodiment of the invention.

The features of this invention can be used both with straight drainage catheters, or with catheters provided with inflatable means for retention of the catheter in the body cavity, such as the Foley-type catheter.

The features of this invention will become understood by reference to a preferred embodiment of the invention illustrated in the accompanying drawings.

BRIEF DESCRIPTION OF THE DRAWINGS

FIG. 3 is a view similar to that shown in FIG. 2 but inverted, and showing how the coupling permits usage to effect back flushing of the catheterized body cavity;

FIG. 3A is a view similar to FIG. 2A, but inverted, and showing how the back flusher shown in FIG. 3 cooperates with the coupling; and FIG. 4 is a fragmentary perspective view of details of the coupling shown in FIGS. 1A, 2A and 3A.

DETAILED DESCRIPTION OF THE INVENTION

Figure 1:
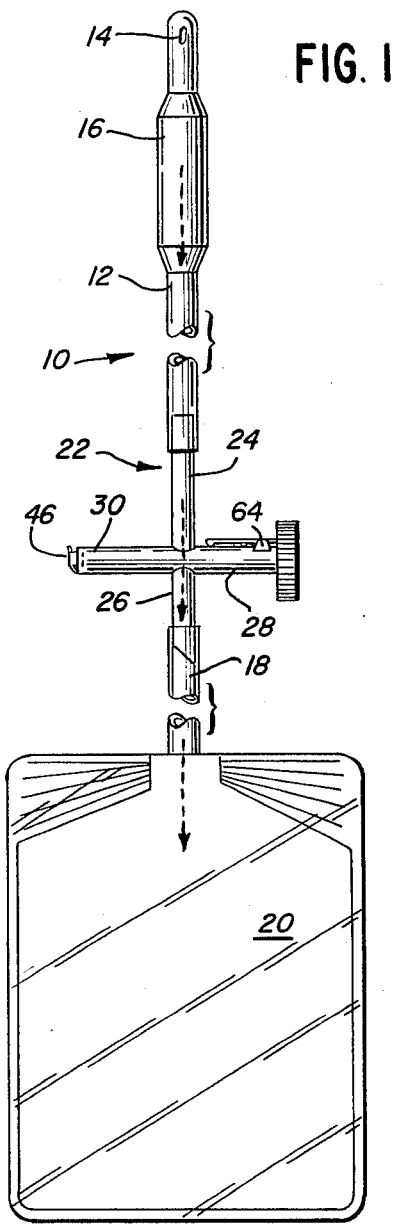
FIG. 1 is a fragmentary view of a typical system of tubes and capture bag for bladder catheterization, and illustrating use of the coupling of this invention in such a system.
Figure 2:
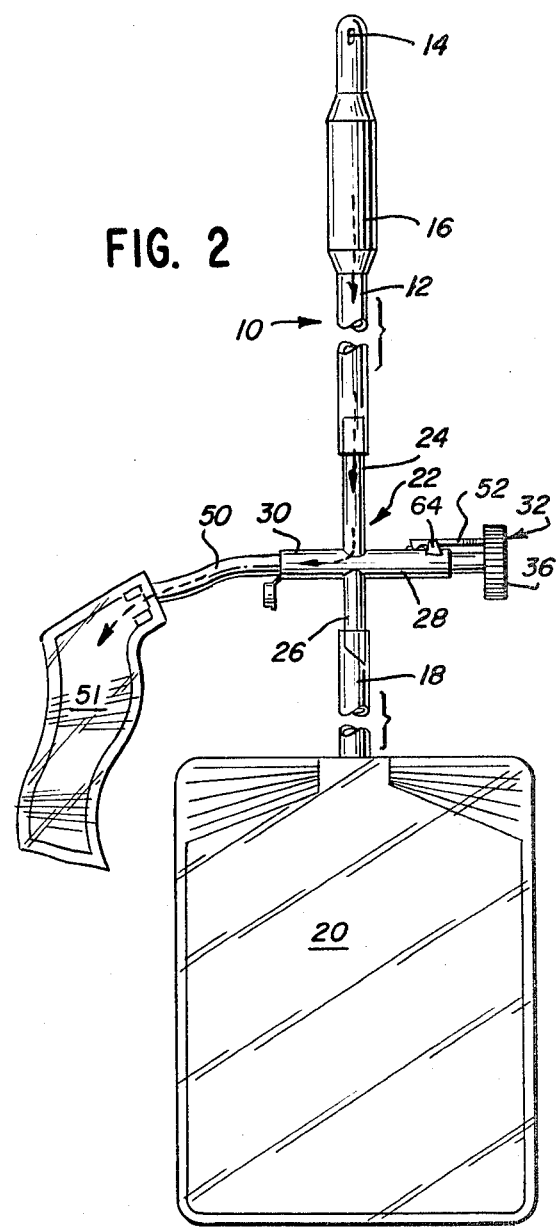
FIG. 2 is a view similar to that shown in FIG. 1, and showing how the coupling of this invention may be used with a means to capture a mid-stream sample of urine.

Referring now to the drawings, what appears generally as a typical catheterization system is generally illustrated at 10, and same includes an elongated, upstream catheter tube means 12 that is shown provided with an entry aperture 14 through the wall adjacent the end of the tube that is to be lodged in a body cavity. On the specific catheter tube means 12 illustrated, there is provided an inflatable collar 16 which, after the tube is properly lodged in a body cavity, may be inflated to prevent withdrawal of the tube means 12, as is well known in the art.

The catheterization system 10 also includes a downstream tube means 18 that leads to and empties into a container for capturing fluid delivered by the system. As is well known in the art, and as preferred in closed systems, the elongated tube means 18 is formed integrally with a bag 20. Normally, there would be a junction tube, between upstream tube means 12 and downstream tube means 18, consisting of a straight length of plastic tubing to which the relatively adjacent ends of the tube means 12 and 18 connect, so that there then exists a through passageway from entry aperture 14 to the interior of capture bag 20.

A portion of the improvement disclosed herein resides in the use of a novel coupling and valving system for the junction tube referred to above. Instead of using a simple flow through tube that must be selectively separated from the end of either tube 12 or 18, so as to break the system and to permit mid-stream sampling of fluid from the body cavity, there is provided the improved construction shown that includes a tubular cross member 22 with four tubular arms arranged in two opposing pairs. A first pair of oppositely extending tubular arms 24 and 26 serve substantially the same function as the usual flow through tube, while the second pair of tubular arms 28 and 30 are at right angles to the axis of tubular arms 24 and 26. The free end of either or both arms 24 and 26 may be beveled, as seen at 26a to provide for ease in effecting a press fit into the associated resilient tube 18. The cross member 22 is an integral molded plastic part.

Figure 1A:
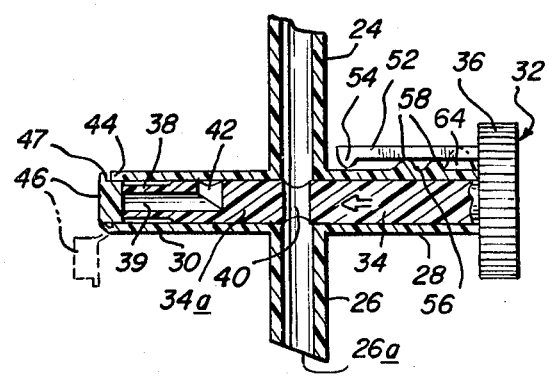
FIG. 1A is a fragmentary enlarged cross-sectional view of the valve illustrated generally in FIG. 1, and shows the position of the coupling parts when the catheterization system is operating to perform its usual function.
Figure 2A:
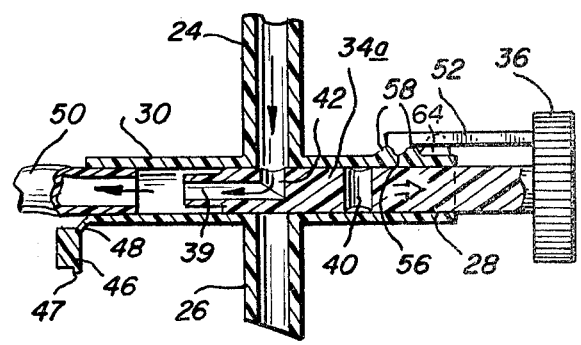
FIG. 2A is a view similar to that shown in FIG. 1A but showing the position of the coupling parts when the system is operating to effect mid-stream sampling of liquid, such as urine, flowing from the body cavity.

The second pair of tubular arms 28 and 30 are axially aligned to serve as projected extensions of each other, and to provide a cylindrical cross passageway in which is positioned an elongated valve member, generally indicated at 32, that is adapted for reciprocating movement substantially between the two positions shown in FIGS. 1A and 2A. The valve member 32, preferably of molded plastic, is best seen in FIGS. 1A, 2A and 3A, and includes an elongated, rod-like, cylindrical valve body 34 with a handle, or control knob, 36 at one end thereof. The opposite end of valve body 34 may be of reduced exterior diameter relative to the inside diameter of arm 30, and is tubular to provide a tubular end portion 38.

Intermediate the ends of the elongated body 34 there is provided a first diametric bore 40 extending through body 34. The bore 40 is spaced axially from control knob 36 such a distance, considering the length of arm 28, that when the knob 36 abuts the terminal edge of tubular arm 28, as seen in FIG. 1A, said diametric bore 40 is located precisely in alignment with the flow passageway defined by the inner diameter of aligned arms 24 and 26.

The exterior diametric size of body 34 is selected so as to fit somewhat snugly against the inner resilient wall of the tubular arms 28 and 30 so as to normally effect a seal against leakage of liquid therebetween, yet at the same time being easily selectively movable between the two positions shown in FIGS. 1A and 2A, and also to an intermediate position between said two positions, merely by moving the body 34 axially through manipulation of control knob 36.

As earlier noted, the end of body 34 opposite handle 36 is a tubular end portion 38. The bore 39 of tubular end portion 38 extends axially, as shown, from the end of body 34 and terminates at a point spaced from bore 40. A second radial bore 42 is provided in body 34, lying parallel to bore 40 but spaced axially from bore 40 away from handle 36, and intersecting bore 39 to provide an angled passageway consisting of bore 42 and bore 39. When the valve member 32 has been moved to the position of FIG. 2A, the second radial bore 42 is aligned with the passageway through tubular arm 24, so as to receive liquid from catheter tube means 12 and to direct the liquid laterally through tubular arm 30, thereby effecting a bypass without any need for separating any of the tubes 12 or 18 from the cross member 22. As illustrated in FIGS. 1A and 2A, the minimum axial spacing of bores 40 and 42 is greater than the inner diameter of tubular arms 24 and 26, so that imperforate body portion 34a could, if desired, be selectively moved to an intermediate position, blocking flow through tubular arms 24 and 26 and through the tubes 12 and 18 to which said arms connect.

When the valve body 34 is in the position shown in FIG. 1A, the tubular end of body member 34 may be spaced axially short of the terminal edge 44 of arm 30. The cross member 22 may be provided with a separate, or integral, closure cap 46, shown in full lines, for entering into and closing the open end of tubular arm 30. If closure cap 46 is integral with cross member 22, it may be connected to tubular arm 30 through a flexible connection strip 48 which serves as a hinge. A tab 47 may be provided on an edge of closure cap 46, located outwardly of tubular arm 30, to provide a means for moving or separating the cap 46 from its closed position, shown in full lines, to be moved to the open position shown in broken lines in FIG. 1A and in full lines in FIG. 2A. The tubular end of body member 34 could be extended to project outwardly of tubular arm 30, and could be protected from contamination by a slip-over cap (not shown) that would fit onto the tubular end of valve body 34. As shown in FIG. 1A, the closure cap 46 serves to prevent contamination from ambient conditions.

When tubular arm 30 is open, as seen in FIG. 2A, the free end of an elongated tube 50 may be introduced into the open end of arm 30, to provide for connection of various accessories to the bypass passageway defined through tubular arm 30. The tube 50 may be press fit into arm 30 as seen in FIG. 2A, or may be of a size to enter the arm 30 and to fit onto the reduced tubular end portion 38 of body 34 shown. As liquid flows in the direction illustrated by the arrows in FIG. 2A, a sample of fluid from the body cavity, such as a sample of urine, will flow from the upstream tubing means 12 through passageway 42–39 and through tubular arm 30 to enter tube 50 that is an integral part of a specimen-capturing container, such as bag 51. When a sufficient sample of fluid has been obtained in bag 51, the valve 34 is moved back to the position shown in FIG. 1A. Thereafter, the tube 50 may be closed, or shut off, with any means known in the art, and withdrawn from arm 30. The catheterization system is now in its normal position for operation without breaking the flow system, or permitting exposure of bore 40 to the possibility of contamination from ambient conditions.

It is desirable to maintain the bores 40 and 42 in proper radial alignment with the passageways defined by tubular arms 24 and 26. Accordingly, means are provided on the valve member 32 and on the tubular cross member 22 to insure proper alignment at all times. Although the shape of valve body 34 and interior of tubular arm 28 could be shaped or keyed to prevent rotation of elongated valve body 34, about its axis, in the preferred construction shown, the control knob 36 is provided with an elongated arm 52 extending parallel to and spaced from valve body 34 with a radially, inwardly-extending, abutment 54 on arm 52 adjacent the extended end of arm 52. The exterior surface of arm 28 is provided with two means for cooperation with arm 52, one to provide a dwell position for abutment 54 and the other to prevent rotation of valve body 34 about its axis.

The dwell position 56 is provided between a pair of ribs or enlargements 58 provided on the exterior of tubular arm 28. When the valve member 32 is in position shown in FIG. 1A, the abutment 54 is free of the dwell position 56. When the valve member 32 is shown in position of FIG. 2A, the abutment 54 enters the dwell position 56 serving as means to hold the valve body in the FIG. 2A position with radial bore 42 in alignment with the tubular arm 24. The arm 52 is flexible, and enlargement 54 may be released from the dwell position by merely lifting up on the free end of arm 52 and pushing the valve member 32 to its position illustrated in FIG. 1A.

To maintain the bores 40 and 42 in the same plane that extends through the bores of arms 24 and 26, the exterior of arm 28 is provided with a pair of spaced ears 64 which bound the plane in which elongated arm 52 is located and is movable, thereby serving to prevent rotation of valve body 34 about its axis.

With the valve body 34 in the position shown in FIG. 2A, not only can flow from a body cavity be diverted from the interior of the body cavity through the tubular arm 30, but the tubular arm 30 also provides a means through which liquid is back flowed, or instruments may be introduced, through the tubular arm 24 and tube means 12 to the interior of the body cavity.

For example, a tubular nipple, or nozzle, 60 that is part of a manually actuatable irrigating 62, may be used to force irrigating liquid in a direction opposite to the normal flow. This back flow, or irrigating flow, is indicated by flow arrows in FIG. 3A. With bore 42 aligned with the passageway through arm 24 of the cross member 22, there may be introduction of either liquid or gas or instruments through tube 24 to the interior of the body cavity. Thus, the construction very conveniently permits of introduction of medication to the body cavity that is catheterized.

While a particular embodiment of this invention has been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What is claimed is:

1. In a urinary catheterization system that includes upstream flexible catheter supply tube means through which captured liquid is ducted, downstream flexible receptor tube and capture means spaced from said upstream tube means and adapted to receive liquid therefrom, and a tubular cross member constructed to define intersecting elongated passageways each partially bounded by a pair of spaced, elongated, open-ended tubular arms of internal cylindrical periphery, said cross member being interposed between said upstream and downstream tube means and providing spaced upstream and downstream tubular arms thereof respectively telescoped with portions of said upstream and downstream flexible tube means to provide separable but liquid tight connections between each tube means and its tubular arm, and with the other pair of opposed tubular arms having an internal cylindrical periphery for receiving therein an elongated, slidable, valve member, of exterior cylindrical periphery, that requires application thereto of a deliberate positive manual force to move said slidable member in either of opposite directions;

the improvement of a multiple position midstream valve, for directing the catheterized urine selectively along either of two completely separate flow paths in the slidable valve member to avoid cross contamination of the urine and/or of the technician handling the equipment and surroundings, comprising, in combination:

said elongated and selectively positionable slidable valve member being shaped and arranged to define a first transverse flow passageway means formed in and through said valve member and extending substantially diametrically of the longitudinal axis of said valve member and at a location spaced axially from both ends of said valve member, and a second flow passageway means in said valve member but spaced axially from said first flow passageway means, said second flow passageway means being shaped to provide a first portion thereof extending radially into the valve member from a terminal opening in the side wall of the elongated valve member, and a second portion thereof communicating with said first portion and extending axially of the valve member to terminate at and through one end of the elongated valve member;

the other end of the elongated valve member projecting axially outwardly of its said surrounding tubular arm and being provided thereat with grippable control means which affords means to effect manual selective axial movement of the valve member for axial positioning of said valve member in said second pair of opposed tubular arms;

said valve member being shaped to provide seal surfaces thereon which slide against and cooperate with the inner periphery of the second pair of tubular arms to prevent liquid flow leakage between the adjacent surfaces of the valve member and the surrounding tubular arms, and which also function to isolate the first and second flow passageways means in the valve member from each other, so as to foreclose cross flow between said flow passageway means; and means operatively associated with said control means of said elongated slide valve member, but spaced from the interior of the tubular arms that surround the slide valve member, and cooperating with means provided integrally on the exterior of said cross member for preventing rotation of the elongated, cylindrical, slide valve member about its longitudinal axis and providing means to precisely selectively position each of the two flow passageway means in the valve member in flow receiving relation relative to the flow supplying passageway through said upstream tubular arm of the cross member.

2. A construction as in claim 1 wherein the elongated valve member is a solid cylindrical body and the first transverse flow passageway is only a diametric bore through the solid cylindrical body.

3. A construction as in claim 1 including means on the valve member and tubular cross member arranged for cooperation to positively locate at least one of the flow passageway means in the valve member in communication with the upstream tubular arm.

4. A construction as in claim 1 including separate means on the valve member and tubular cross member arranged for cooperation to positively locate each of the flow passageway means in the valve member selectively in communication with the upstream tubular arm of the tubular cross member.

5. A construction as in claim 1 wherein said grippable control means is of greater dimension than the axial opening through said second pair of opposed sleeves, so that a portion of said control means is of size and position adapted to abut the adjacent end of the second pair of opposed sleeves to limit movement of the elongated valve member in one direction;

there being formed on the exterior of the one sleeve, of said second pair of opposed sleeves, that is adjacent said control means, a dwell-position defining means and an adjacent pair of spaced ears;

an elongated arm extending from said control means and positioned radially outwardly of the opposed sleeves in which the elongated valve member is positioned, and being shaped adjacent its extended end with an enlargement that is adapted to cooperate with said dwell-position defining means, and with said arm being of a size and shape to project from the control means substantially parallel to the elongated valve member and to pass between said pair of spaced ears to provide an aligning relationship therewith that operates to prevent rotation of the elongated valve member about its longitudinal axis;

the radial flow passageways in said elongated valve member being arranged relative to said control means and to said dwell-position defining means so that when the control means abuts said adjacent sleeve end, the first flow passageway means in said valve member is aligned with the passageway through said one pair of opposed sleeves of the cross member, and with said elongated arm being located between said ears to restrain said elongated valve member from rotation about its axis, and when said elongated arm is in position to have its enlargement seated in the dwell-position, then said radial portion of the second flow passageway means is aligned with the upstream flow passageway of said one pair of opposed sleeves of the cross member, and with said arm positioned between the pair of spaced ears to restrain the valve member from rotation about its axis.

6. A construction as in claim 1 wherein said one end of the elongated valve member is always positioned within and spaced axially short of the terminal edge of one of the other pair of tubular arms, and a closure cap that is operatively associated with the said terminal edge of the said one tubular arm for selectively closing or opening the said terminal edge of said tubular arm.

7. A construction as in claim 1 wherein the one end of the valve member is shaped to provide a tubular extension whose exterior diameter is less than the inner diameter of the adjacent tubular arm of the tubular cross member.

8. A construction as in claim 7 wherein the tubular extension on the valve member is positioned concentrically within the adjacent tubular arm of the tubular cross member, to provide an annular space between said tubular arm and tubular extension of a size to sealingly receive thereinto a tubular member.

9. A construction as in claim 7 wherein the size and shape of the tubular extension of the valve member and the adjacent tubular arm of the cross member are selected so as to permit entry of a nozzle through which to effect back flushing or irrigation through said tubular extension, the second flow passageway, and the upstream flow tube means.

* * * * *